(12) United States Patent
Crawford, Jr. et al.

(10) Patent No.: US 7,654,802 B2
(45) Date of Patent: Feb. 2, 2010

(54) RECIPROCATING DRIVE APPARATUS AND METHOD

(75) Inventors: Richard William Crawford, Jr., Yucaipa, CA (US); Fang Zheng, Irvine, CA (US); Charles Edward Beuchat, Irvine, CA (US)

(73) Assignee: Newport Medical Instruments, Inc., Costa Mesa, CA (US)

( * ) Notice: Subject to any disclaimer, the term of this patent is extended or adjusted under 35 U.S.C. 154(b) by 715 days.

(21) Appl. No.: 11/315,608

(22) Filed: Dec. 22, 2005

(65) Prior Publication Data

US 2007/0148016 A1 Jun. 28, 2007

(51) Int. Cl.
*F04B 17/00* (2006.01)
*F16H 25/08* (2006.01)

(52) U.S. Cl. ............... 417/415; 417/273; 417/419; 74/44; 74/45; 74/46; 74/50; 74/53; 74/55

(58) Field of Classification Search .......... 417/273, 417/415, 419; 74/44, 45, 46, 47, 49, 50, 74/53, 55; 123/55.5; 384/45; 70/44, 45, 70/46, 49, 50, 53, 55
See application file for complete search history.

(56) References Cited

U.S. PATENT DOCUMENTS

| 122,502 | A | 1/1872 | Wallace |
|---|---|---|---|
| 124,805 | A | 3/1872 | Fryer |
| 129,996 | A | 7/1872 | Swenson |
| 285,178 | A | 9/1883 | Taylor |
| 297,482 | A | 4/1884 | Wilson |
| 575,720 | A | 1/1897 | Ledent |
| 947,233 | A * | 1/1910 | Hammond ............ 74/49 |
| 1,293,766 | A | 2/1919 | Hammond |
| 2,328,918 | A | 9/1943 | McManus |
| 3,200,800 | A | 8/1965 | Du Bois |

(Continued)

FOREIGN PATENT DOCUMENTS

FR 651805 2/1929

(Continued)

OTHER PUBLICATIONS

International Preliminary Report on Patentability with Written Opinion of the International Searching Authority from related PCT/US2006/062237, dated Jun. 24, 2008.
International Search Report for PCT/US06/62237.

*Primary Examiner*—Devon C Kramer
*Assistant Examiner*—Leonard J Weinstein
(74) *Attorney, Agent, or Firm*—Procopio, Cory, Hargreaves & Savitch LLP

(57) ABSTRACT

A reciprocating drive apparatus has a driving device and a driven device, one of the devices comprising a reciprocating member mounted for movement along a longitudinal axis. At least one rotary member is coupled to one of the devices and a linear bearing assembly has a linear guide rail and a linear slide member with an end coupled to the other device. A connecting link has a first end pivotally connected to the rotary member and a second end pivotally linked to the slide member. Where the reciprocating member is the driven device, rotation of the rotary member will cause the reciprocating member to move back and forth along the longitudinal axis.

13 Claims, 9 Drawing Sheets

U.S. PATENT DOCUMENTS

| | | | |
|---|---|---|---|
| 3,886,805 A | 6/1975 | Koderman | |
| 4,419,904 A | 12/1983 | Albury | |
| 4,485,768 A * | 12/1984 | Heniges | 123/48 B |
| 4,524,583 A | 6/1985 | Scheibengraber | |
| 4,559,838 A * | 12/1985 | Neuenschwander | 74/50 |
| 4,590,812 A * | 5/1986 | Brackett | 74/55 |
| 4,779,472 A * | 10/1988 | Brackett | 74/50 |
| 4,915,019 A * | 4/1990 | Hovaguimian | 92/136 |
| 4,995,277 A * | 2/1991 | Yanagisawa | 74/490.09 |
| 5,092,185 A * | 3/1992 | Zornes et al. | 74/50 |
| 5,503,038 A * | 4/1996 | Aquino et al. | 74/49 |
| 5,582,487 A | 12/1996 | Teramachi | |
| 5,655,406 A * | 8/1997 | Yanagisawa | 74/50 |
| 5,762,480 A | 6/1998 | Adahan | |
| 5,836,751 A | 11/1998 | De Villiers | |
| 5,943,987 A * | 8/1999 | Fischer | 123/55.5 |
| 6,539,835 B1 * | 4/2003 | Rasmussen | 92/140 |
| 6,631,671 B1 * | 10/2003 | Vool | 92/165 R |
| 7,004,522 B2 * | 2/2006 | Nagai et al. | 294/64.1 |
| 2005/0139021 A1 | 6/2005 | Shuhua | |

FOREIGN PATENT DOCUMENTS

| | | |
|---|---|---|
| GB | 431237 | 7/1935 |
| WO | WO 00/37827 | 6/2000 |

\* cited by examiner

RECIPROCATING DRIVE APPARATUS AND METHOD

BACKGROUND OF THE INVENTION

This application is directed to a reciprocating drive apparatus for converting rotary motion into linear motion, or vice versa.

Reciprocating drives for converting between rotary and linear motion may be used, for example, to drive the piston of a pump in various different types of machine. Air pumps are commonly used for ventilators in the medical field, but there are major challenges inherent in using a reciprocating drive to actuate such pumps. For example, such pumps, which are required to deliver clean air, cannot use lubricants between the piston and cylinder. They must also be sufficiently small to fit into the equipment. This means that any offset from a true linear motion is more critical and can cause side loads which will eventually lead to failure of the pump.

U.S. Pat. No. 5,762,480 describes one reciprocating machine which has been used to drive an air pump. This machine uses a four bar linkage mechanism to convert the rotary motion of the drive motor into a linear movement to operate the pump. This does not deliver a true linear motion, due to the nature of the linkage mechanism, and this results in side load to the seal diaphragms and the pump cylinder or cylinders. This could eventually result in air leakage and component failure.

SUMMARY OF THE INVENTION

It is an object of the present invention to provide a new and improved reciprocating drive apparatus.

According to one aspect of the present invention, a reciprocating drive apparatus is provided, which comprises a rotational drive, at least one rotary member or crank shaft having a first portion linked to the rotational drive for rotation about an axis of rotation, and a second portion offset from the axis of rotation for rotating in a circular path about the axis of rotation, a fixed linear bearing rail, a linear bearing slide member slidably mounted for reciprocal movement along the guide rail between opposite end positions, and a link arm having a first end rotatably linked to the second portion of the rotary member and a second end rotatably linked to the linear slide member, whereby rotation of the second portion of the rotary member about the circular path forces the linear slide member to slide back and forth between the end positions.

Since the slide member is constrained to move along a linear bearing rail, side loading on a member to be driven by the slide member is reduced or eliminated.

In an exemplary embodiment, the slide member is linked to the piston of a pump via a piston rod for driving the pump back and forth in its cylinder. The piston rod passes through a close tolerance diaphragm seal into the cylinder, where it is connected to the piston. The linear bearing slide is constrained within the bearing rail so that it moves back and forth along a linear path, so that any potential side load on the piston rod as a result of the rotational drive is reduced or eliminated. This also reduces the risk of potential damage to the diaphragm seal and cylinder as a result of side loads.

The components of the apparatus, including the pump, may be contained in a single housing. The apparatus may be used, for example, in a medical ventilator, an oxygen concentrator, a suction pump for medical and other applications, or for a pump in a vehicle such as an automobile or airplane.

In one embodiment of the invention, two pumps are included and each pump has a piston with a drive shaft, one of the drive shafts being connected to one end of the slide member and the other drive shaft being connected to the other end of the slide member, so that one piston is in the advanced position while the other is retracted, and vice versa. In another embodiment, the rotational drive or motor may have two oppositely directed drive shafts with a first rotary member connected to one drive shaft and a second rotary member connected to the other drive shaft, and first and second linear slide members each linked to a respective rotary member by a respective link arm. Each slide member may be linked to one or two pistons, such that a maximum of four pumps may be operated by the apparatus.

In an exemplary embodiment of the invention, the linear guide rail and slide member together comprise a linear bearing set, and the guide rail is fixed to the outer housing with bolts or the like to hold it stationary and resist any movement of the rail. The linear slide member may have a groove or channel for slidably engaging over the rail, with suitable interengaging formations between the rail and slide member to hold the slide member on the rail.

According to another aspect of the present invention, a method of converting rotational motion to linear motion is provided, which comprises the steps of: connecting the output of a rotational drive to one end of a crank shaft, rotatably linking the opposite end of the crank shaft to one end of a link member, rotatably linking the opposite end of the link member to a slide member slidably mounted on a linear bearing rail for movement back and forth in a linear path, whereby rotation of the crank shaft through one complete revolution drives the slide member back and forth between opposite end positions, and connecting the slide member to an object to be driven back and forth in a linear path.

The slide member may be connected to a piston rod which extends through a sealed opening into a cylinder of a pump or the like, and is connected to a piston slidably mounted in the cylinder. Opposite ends of the slide member may each be connected to a piston rod, each piston rod extending into a respective pump cylinder for driving a piston back and forth in the cylinder. The rotational drive may be connected to two oppositely directed crank shafts, each crank shaft being rotatably linked to a respective slide member which is slidably mounted on a respective linear bearing slide, and each slide may be connected to a piston rod extending into a respective pump cylinder for actuating a piston in the respective cylinder, to provide a two piston pump arrangement. If each slide is connected to two oppositely directed piston rods extending into two pump cylinders for actuating the pistons in the respective cylinders, a four piston pump arrangement is provided.

According to another aspect of the present invention, a reciprocating pump assembly is provided, which comprises a housing, at least one cylinder in the housing, a piston slidably mounted in the cylinder, a piston rod extending from the piston out of a first end of the cylinder, a linear slide rail secured in the housing adjacent the first end of the cylinder to extend in a direction parallel to the direction of travel of the piston and piston rod, a slide member slidably mounted on the slide rail in alignment with the axial direction of travel of the piston and rigidly secured to the piston rod, a rotational drive in the housing having a crank shaft extending towards the slide rail and slide member, and a link member having one end rotatably connected to the crank shaft and the other end rotatably linked to the slide member, whereby rotation of the crank shaft forces the slide member to move back and forth along the slide rail between opposite end positions and to actuate the piston to slide back and forth in the cylinder.

In an exemplary embodiment of the invention, a second piston and cylinder are provided in the housing, and the rotational drive has a second crank shaft extending in the opposite direction to the first crank shaft. The second piston has a piston rod extending out of a first end of the cylinder. A second slide rail is rigidly mounted in the housing to extend in a direction parallel to the axial direction of movement of the piston, and a second slide member is slidably mounted on the rail and rigidly connected to the second drive member. A second link member is rotatably linked at one end to the second crank shaft and at the other end to the second slide member. Rotation of the two crank shafts will simultaneously cause both pistons to reciprocate in their respective cylinders.

The pump assembly may be provided with four cylinders each with a piston slidably mounted in the cylinder. In this case, the third and fourth cylinders will be aligned with the first and second cylinders, respectively, on the opposite side of the first and second slide rails from the first and second cylinders. Piston rods extending form the third and fourth cylinders are linked to the opposite ends of the first and second slide members from the first and second piston rods. Rotation of the two crank shafts in this case will simultaneously cause all four pistons to reciprocate in their respective chambers.

The reciprocating drive apparatus of this invention uses a linear bearing slide rail and slide member in order to convert rotary motion to linear motion with substantially no side loads. When used in the pump assembly of this invention, it can deliver linear motion to one or more pistons. The piston rods extend through diaphragm seals into the respective cylinders, and the lack of any substantial side loads with this apparatus will extend the lifetime of the seals. The linear drive which has little or no side loading also allows the piston to be operated more easily and smoothly without lubrication, as is required for pumps in medical applications.

BRIEF DESCRIPTION OF THE DRAWINGS

The present invention will be better understood from the following detailed description of some exemplary embodiments of the invention, taken in conjunction with the accompanying drawings, in which like reference numerals refer to like parts, and in which.

DETAILED DESCRIPTION OF THE DRAWINGS

Figure 1:
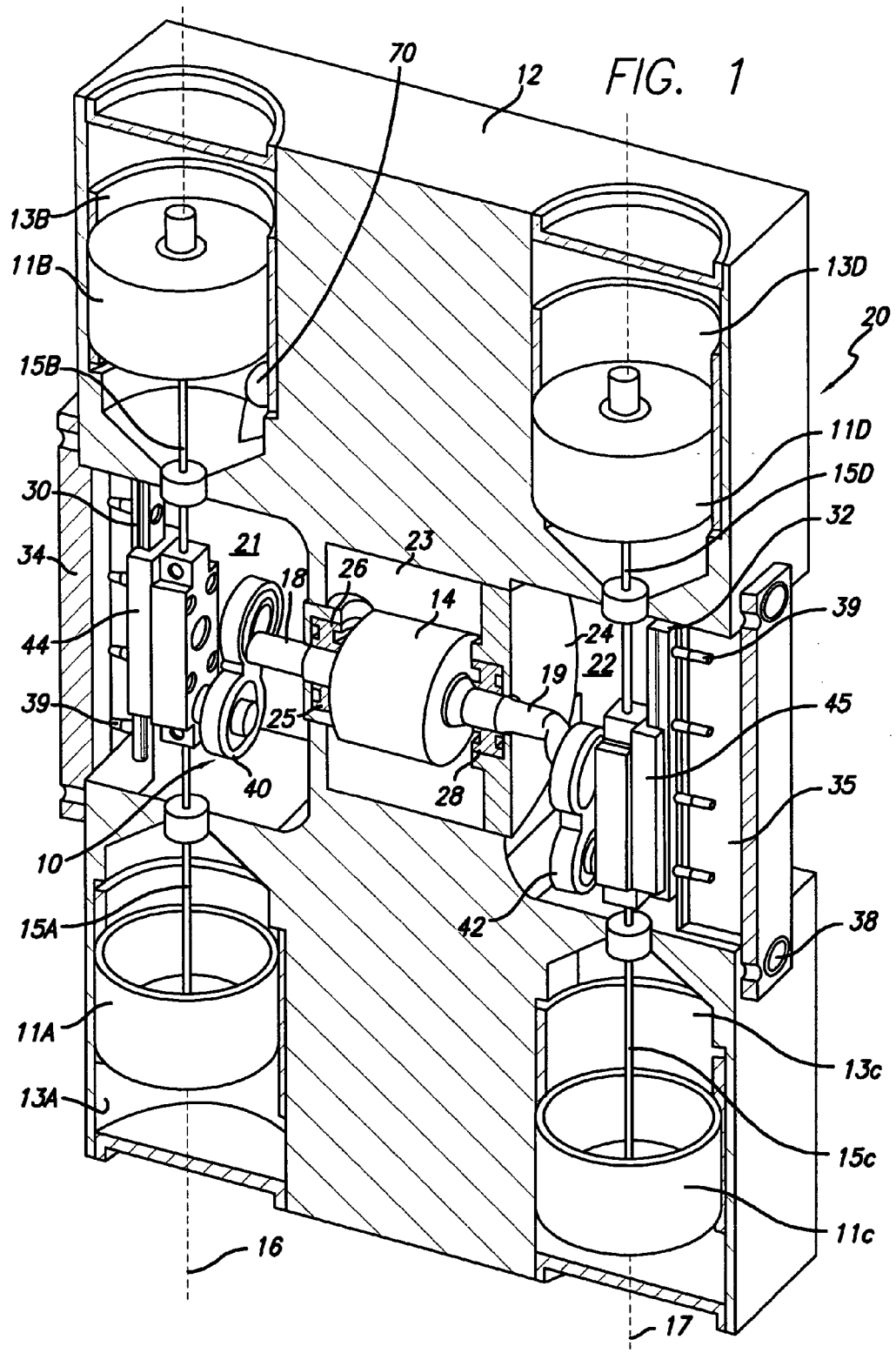
FIG. 1 is a perspective view, partially cut away, of a four piston reciprocating pump assembly incorporating a reciprocating drive apparatus according to an exemplary embodiment of the present invention.

FIGS. 1 to 5 of the drawings illustrate a reciprocating drive apparatus 10 according to an exemplary embodiment of the invention in a four piston pump assembly 20. It will be understood that the reciprocating drive apparatus of this invention may alternatively be used to drive the piston of a single piston pump in other applications, or may be used to convert rotational to linear motion, or vice versa, for other possible purposes. However, in the exemplary embodiment of FIGS. 1 to 5, the apparatus 10 drives four pistons 11A, 11B, 11C and 11D of a four piston pump in a single outer housing 12, and the pump assembly may be designed to pump any fluid, but is particularly intended for use in pumping gases such as air or oxygen in medical applications.

Each piston 11A-D slides in a respective cylinder 13A-D in the housing and is linked to the drive apparatus by a piston rod 15A-D. The pistons and cylinders are arranged in aligned, opposing pairs on opposite sides of the drive apparatus, with one pair being aligned along drive axis 16 and the second pair being aligned along drive axis 17.

Figure 4:
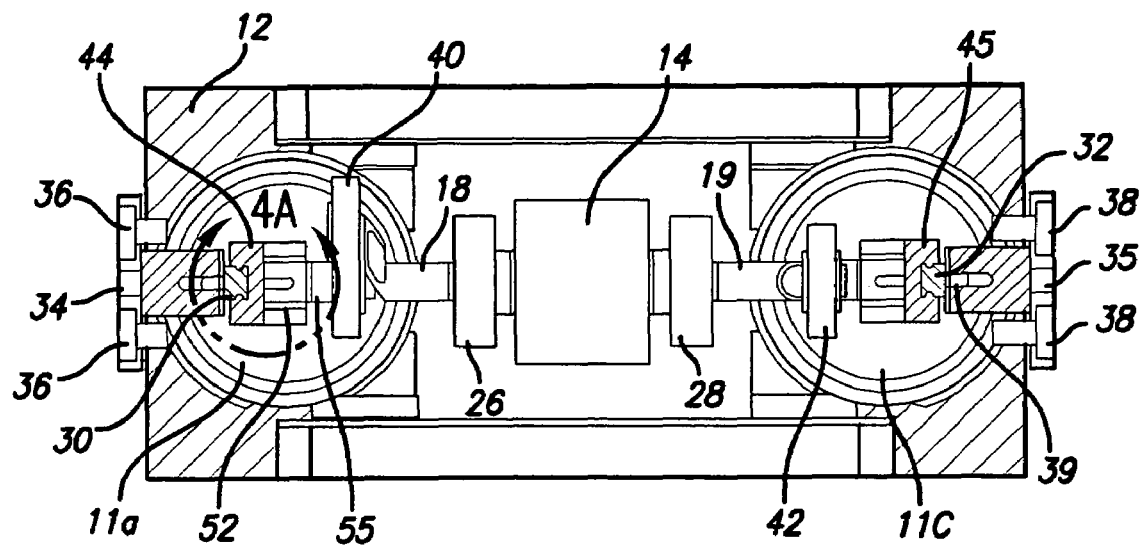
FIG. 4 is a horizontal cross-section through the drive apparatus on the lines 4-4 of FIG. 2.

The reciprocating drive apparatus 10 is mounted in the central region of housing 12, between two opposing pairs of pumps. The apparatus 10 includes a rotational drive or motor 14 in a central chamber 23 with crank shafts or drive shafts 18, 19 projecting from opposite ends of motor 14. A pair of chambers 21,22 are located on opposite sides of the central drive chamber 23, and the crank shafts 18,19 project through opposite end caps 24,25 and rotary bearings 26,28 into the respective chambers 21,22. A linear bearing comprising a linear bearing slide rail 30, 32 and an associated linear bearing slide member 44, 45 is mounted in each chamber. Each slide rail 30,32 is rigidly mounted in each chamber 21,22 facing the crank shaft by means of a respective rigid mounting plate 34,35 which is secured to the outer surface of housing 12 by bolts 36,38. The slide rails are rigidly secured to the inner end faces of the respective mounting plates by bolts 39. The mounting plates each have an outer mounting flange which is bolted to an outer face of the housing, as illustrated in FIG. 4, and a mounting block which extends inwardly into the respective chamber 21,22 to provide a mounting surface for the respective slide rail. This mounting arrangement is extremely strong and secures the linear slide rails or bearing rails rigidly to the housing with no freedom of movement.

Figure 4A:
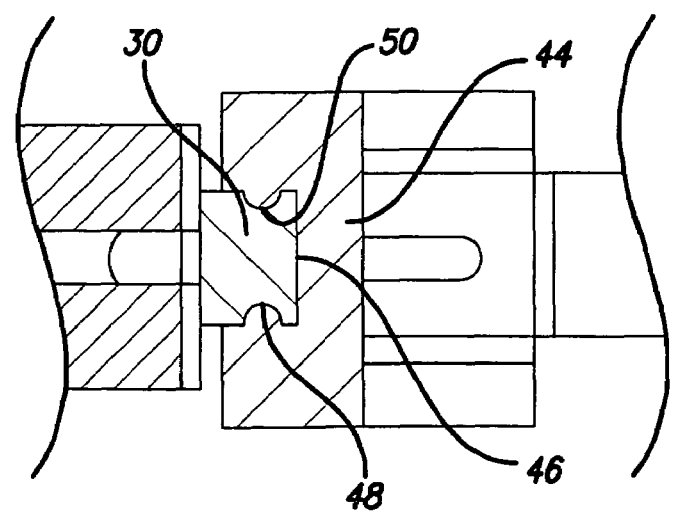
FIG. 4A is an enlarged view of part of the circled portion of FIG. 4, illustrating the engagement of the slide member on the linear slide rail in more detail.
Figure 5:
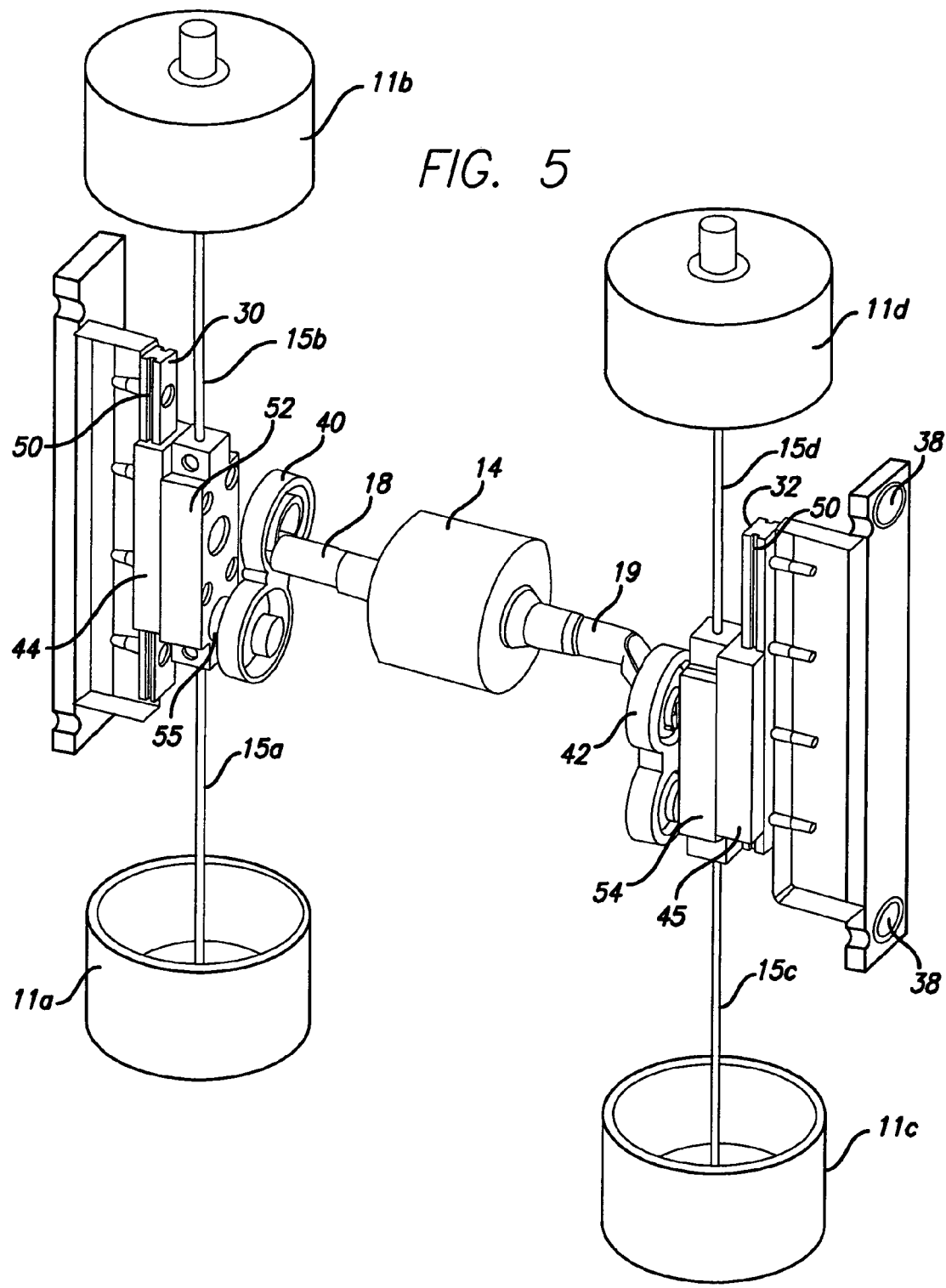
FIG. 5 is a perspective view of the assembly of FIGS. 1 to 4 with the housing removed and with the mounting plate for the slide rail on the right hand side cut away to reveal details of the linear bearing rail and slide.

A connecting link or lever 40,42 is rotatably secured to the offset end of the respective crank shaft 18,19 at one end, and is rotatably linked to the respective linear bearing slide member 44,45 at its opposite end. Each linear bearing may be of the type used in sliding drawers and the like. The engagement between each slide rail 30,32 and the respective slide member 44,45 is illustrated in more detail in FIG. 4A. Each slide member is generally C-shaped to form a channel or groove 46 which engages over the slide rail, with rounded ribs 48 running along the side walls of the channel for engagement in smooth linear raceways or grooves 50 on the opposite sides of the slide rail 30, 32. This arrangement vertically constrains the respective slide members to run in a linear path along the linear bearing rails or slide rails. The linear bearing rail may alternatively be of the type having ball channels in which balls are moved, with the slide member having corresponding ball channels which cooperate with the ball channels on the rail to sandwich a plurality of balls between the ball channels, with end caps to secure the balls in the channels.

In an exemplary embodiment of the invention, the linear bearing sets 30, 44 and 32, 45 each comprise a miniature linear bearing. One example of a suitable miniature linear bearing is the C-sleeve Linear Way ML type, Part No. MLC5C2R55HS2 manufactured by IKO Nippon Thompson Co. of Tokyo, Japan.

Figure 2:
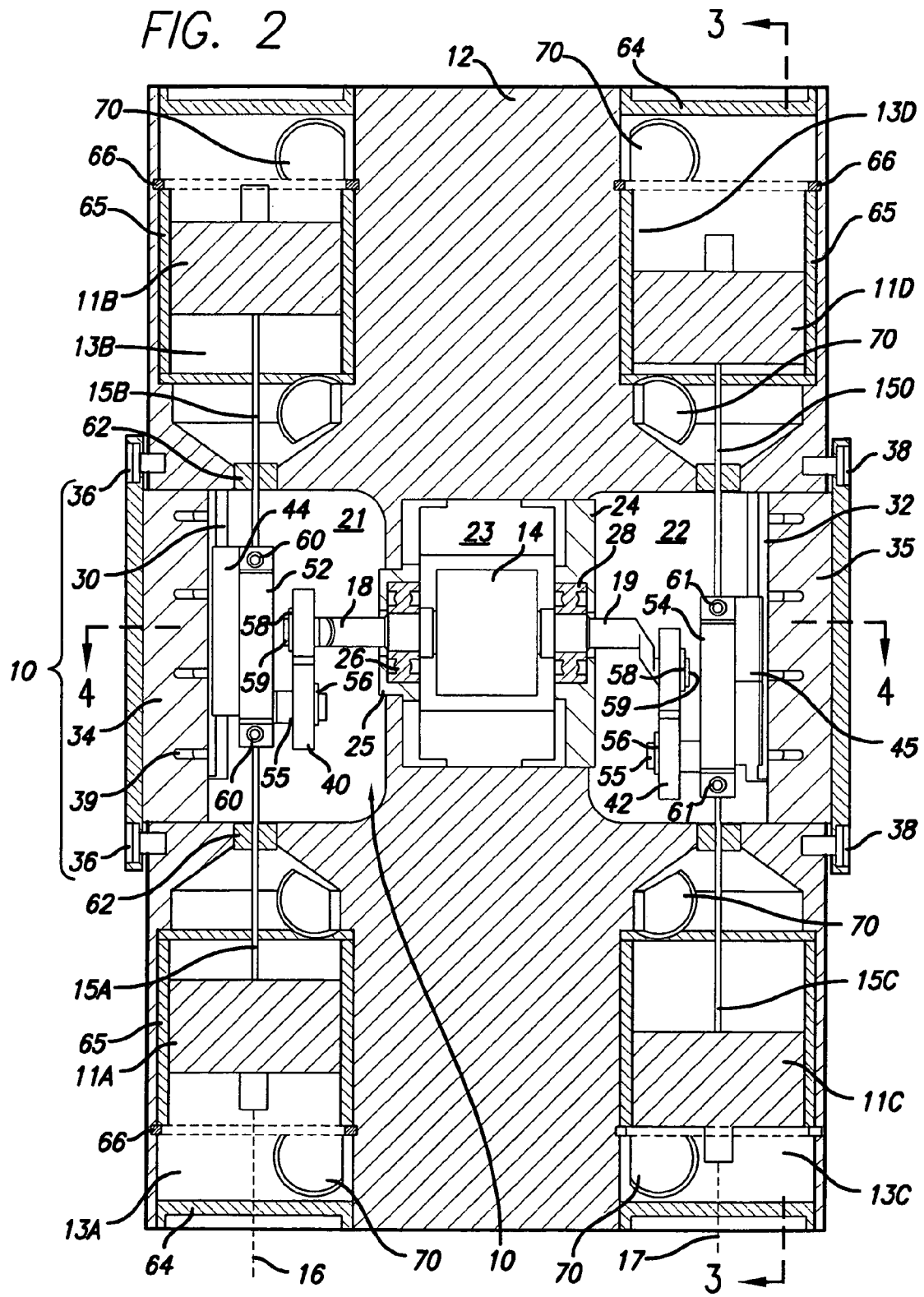
FIG. 2 is a vertical cross-section through the assembly of FIG. 1.

A separate connecting plate 52, 54 is bolted to the outer surface of each slide member 44, 45, and the respective connecting link is rotatably connected to one end of the respective connecting plate 52, 54 on its outer face by pivot pin 55, with a snap ring 56 on the outer end of the pin to keep the bearing in place, as illustrated in FIG. 2. A similar snap ring 58 is mounted on the outer end of pivot pin 59 which rotatably connects the outer end of the respective crank shaft 18,19 to the respective connecting link. The respective pivot pins are rotatably connected to the connecting links via ball bearings or rotary bearings 57, as seen in the schematic illustrations of FIGS. 7 to 9, for smooth operation.

The first connecting plate 52 is rigidly connected at one end to the first piston rod 15A via a first set screw 60, and the opposite end of the plate is rigidly connected to the end of the second, aligned piston rod 15B via a second set screw 60. Similarly, the second connecting plate 54 is connected to the ends of the aligned piston rods 15C and 15D by set screws 61. This arrangement ensures that the piston rods will follow the movement of the linear slide member 44, 45. Each slide rail 30,32 is secured in the housing so as to extend parallel to the axes 16,17 of movement of the two aligned pairs of pistons, and the connecting plates 52 and 54 have central longitudinal axes which are aligned with the respective axes 16,17. This ensures that movement of the slide members 44,45 along the slide rails will simultaneously move the piston rods in a linear path along the axes 16,17.

Although the linear bearing slide member and connecting plate are separate elements which are bolted together in the illustrated embodiment, they may alternatively be formed from one solid block. In either case, the slide member is elongate in the direction of the reciprocating axis, and has an inner channel portion forming part of a linear bearing which engages over the linear bearing rail and an outer, solid portion which is aligned with the longitudinal axis of travel of the piston or pistons.

Figure 3:
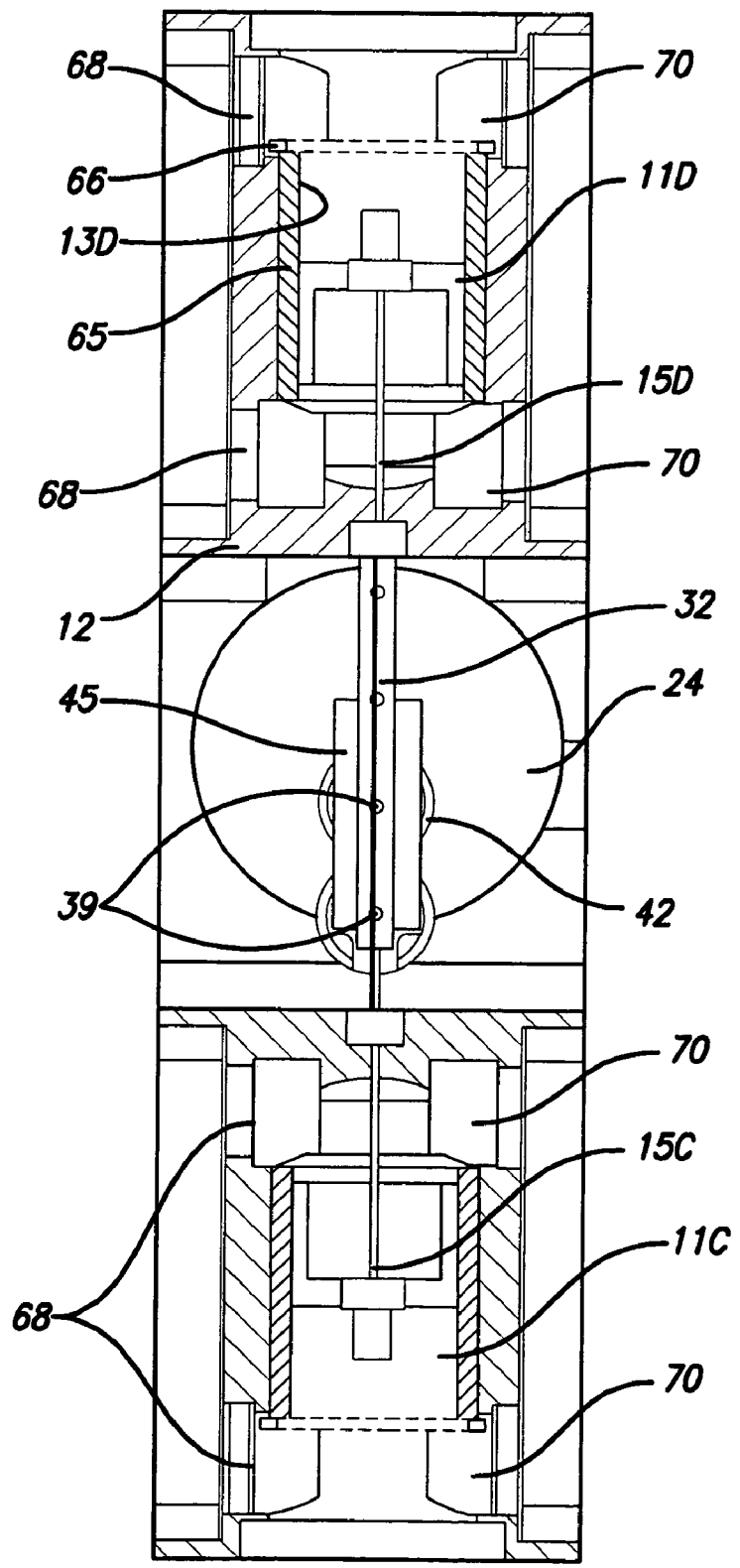
FIG. 3 is a cross section on the lines 3-3 of FIG. 2.

Each piston rod 15 extends through a diaphragm seal 62 into the respective cylinder 13 and is fixed to the respective piston. The internal diameter of each seal is arranged such that the piston can pass through the seal with its outer surface in sealing engagement with the seal, so that no fluid can leak past the seal. The opposite end of each cylinder is sealed by an end cap 64. A glass tube 65 of Pyrex® or the like is secured in each cylinder and is retained in position against a shoulder in the cylinder by a retaining ring 66. The respective pistons travel in the glass tube which has a smooth surface to avoid the need for lubricants. The pistons may be made of graphite to further ensure a smooth sliding motion. As best illustrated in FIG. 3, the chambers on each side of the respective pistons 11 each have a one way inlet check valve 68 on one side for fluid intake and a one way outlet check valve 70 on the other side for fluid delivery. In the case of an air pump for medical uses, the reciprocating linear motion of the four pistons generates air and delivers air via the one way check valves. For example, as the piston 11A moves in a direction towards the end cap 64, air in the lower chamber will be forced out of the chamber via the outlet check valve 70 in that chamber and air will simultaneously be drawn into the upper chamber via its inlet check valve 68, ready for the next cycle.

Operation of the reciprocating drive apparatus 10 will now be described in more detail. As the crank shafts 18,19 rotate, the associated connecting lever or link 40,42 will urge the connecting plate 52,54 and attached slide members 44,45 up and down (as viewed in FIGS. 1 and 2). The slide members are constrained to move in linear paths along the two linear bearing slide rails 30,32. This movement will simultaneously urge the associated pistons to reciprocate back and forth in the respective cylinders, with one complete cycle back and forth for each 360 degree rotation of the associated crank shaft. The two crank shafts are offset to coordinate air flow through the respective exhaust valves, so that a constant air supply is provided. FIG. 2 illustrates the relative positions of the four pistons at one point in the cycle. In this position, the two pistons 11A and 11B are at a central position in their travel in the respective cylinders. The piston 11C is at the outer end of its travel, with air drawn into the upper chamber and delivered out of the lower chamber. The upper piston 11D is at the innermost point in its travel, closest to the drive chamber 22, with air drawn into the outer chamber adjacent end cap 64 and air delivered out of the inner chamber adjacent diaphragm seal 62.

Figure 6:
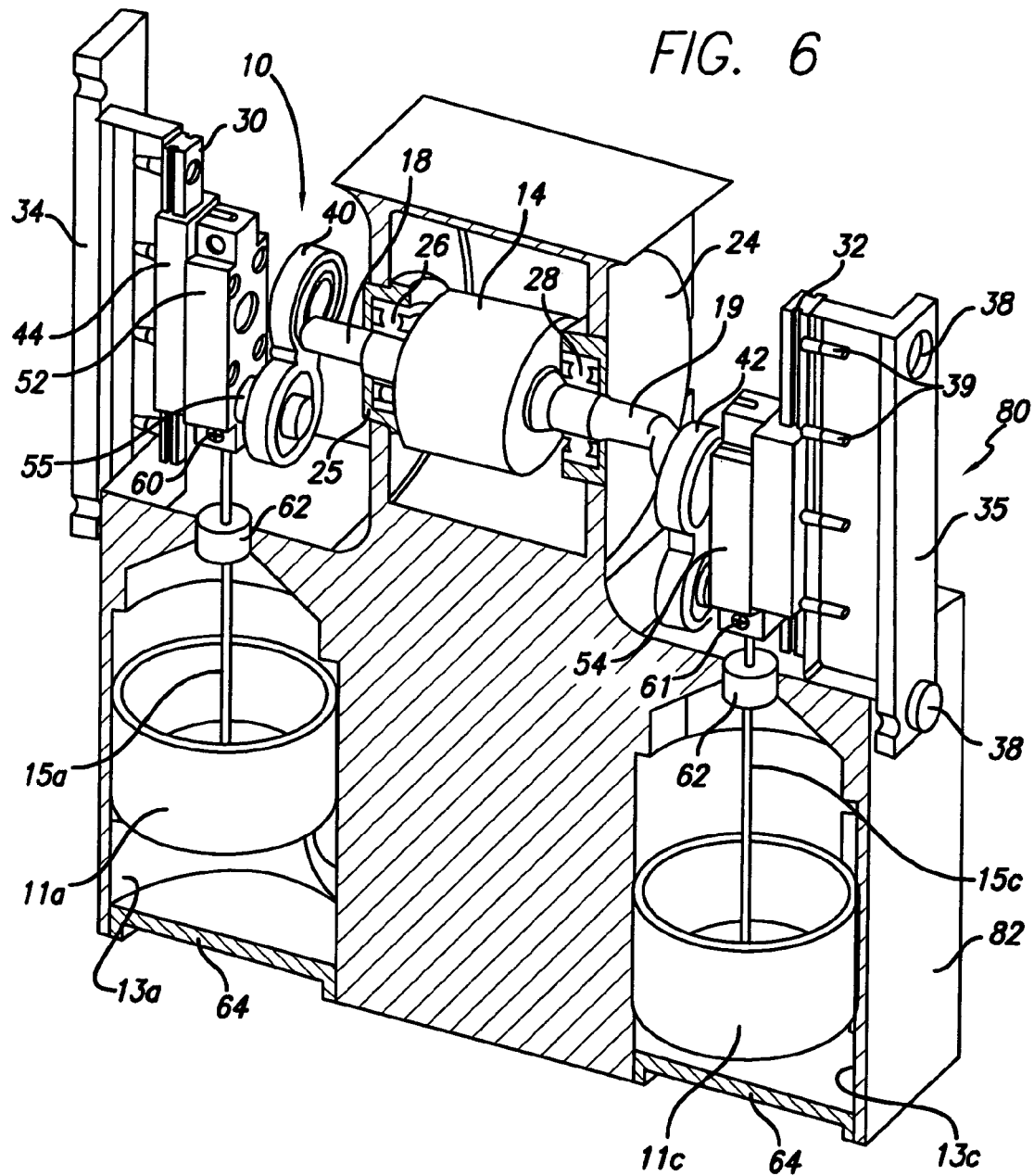
FIG. 6 is a cut away perspective view similar to FIG. 1 illustrating an alternative two piston pump assembly layout.

FIGS. 1 to 5 illustrate a four piston pump. FIG. 6 illustrates an alternative two piston pump assembly 80 which may be adequate in some applications. In this embodiment the upper two pistons and associated cylinders of the first embodiment are eliminated, along with the associated upper portion of housing 12. This embodiment is otherwise identical to that of FIGS. 1 to 5 and like reference numerals are used for like parts as appropriate. In this embodiment, each connecting plate 52,54 is connected to only one piston rod, 15A and 15C, respectively, at one of its ends. The operation is otherwise identical to that of the first embodiment.

Figure 7:
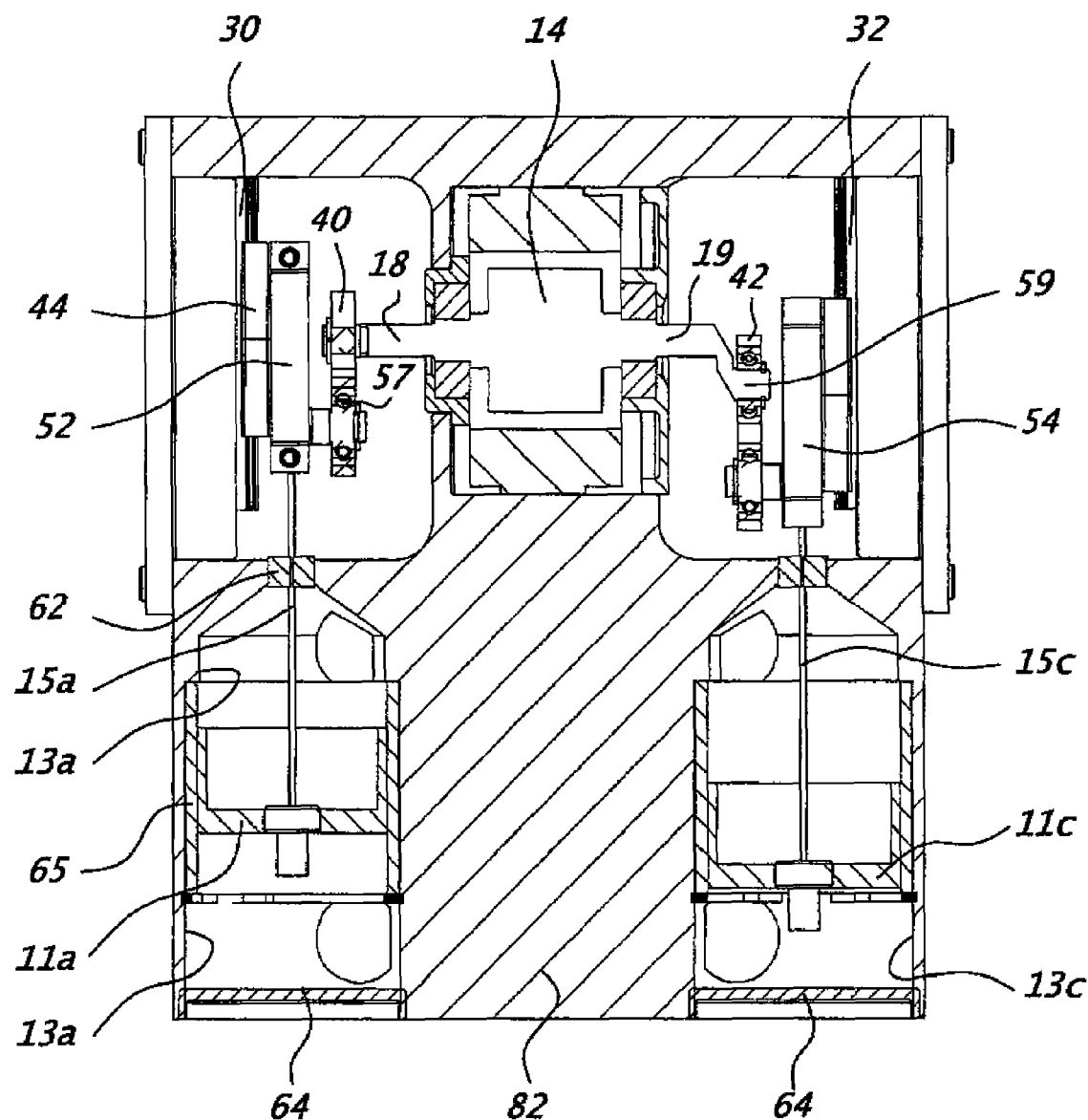
FIG. 7 is a schematic, simplified cross-sectional view of the two piston pump assembly in a first position.
Figure 8:
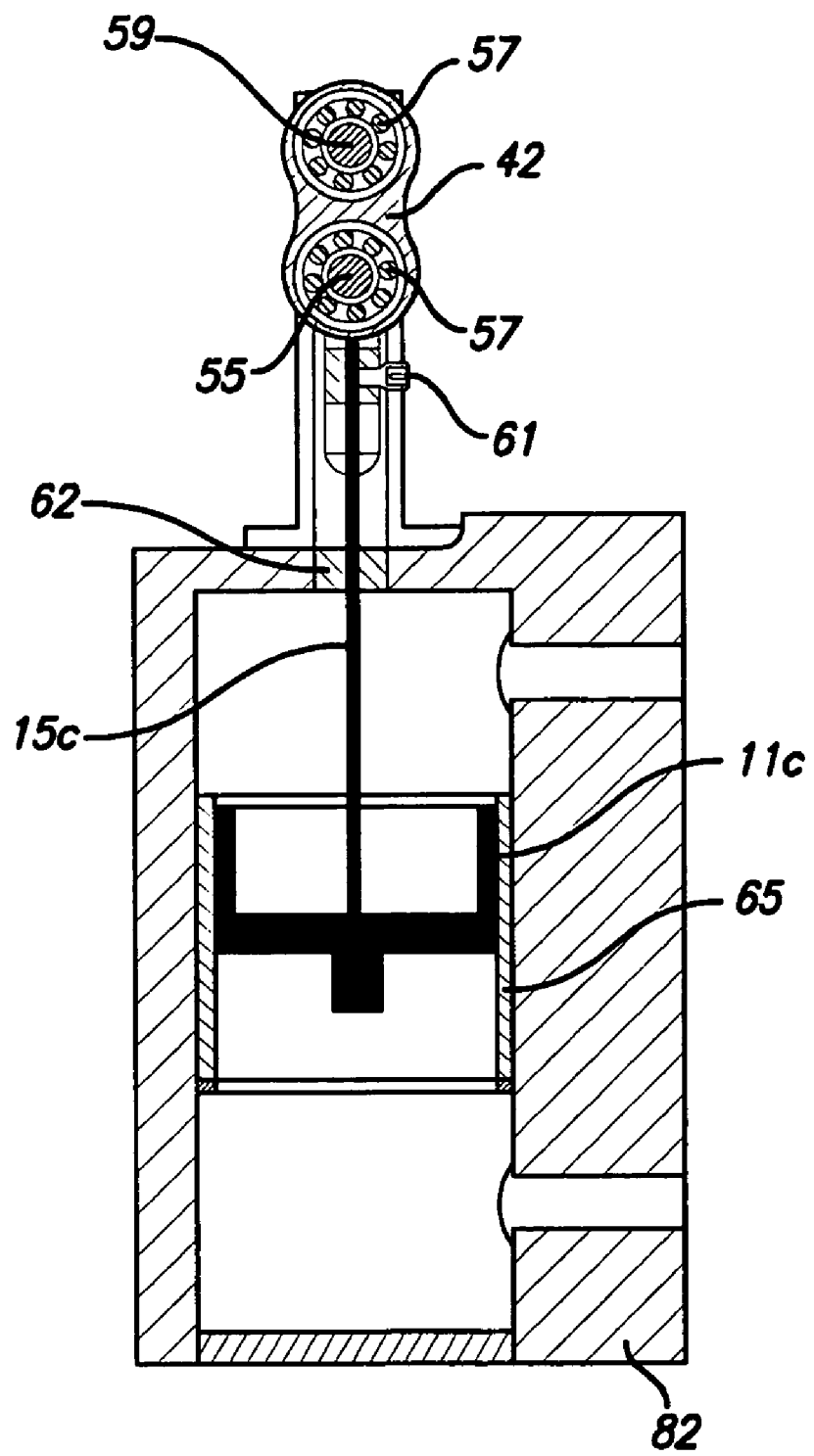
FIG. 8 is a cross-sectional view on the lines 8-8 of FIG. 7.
Figure 9:
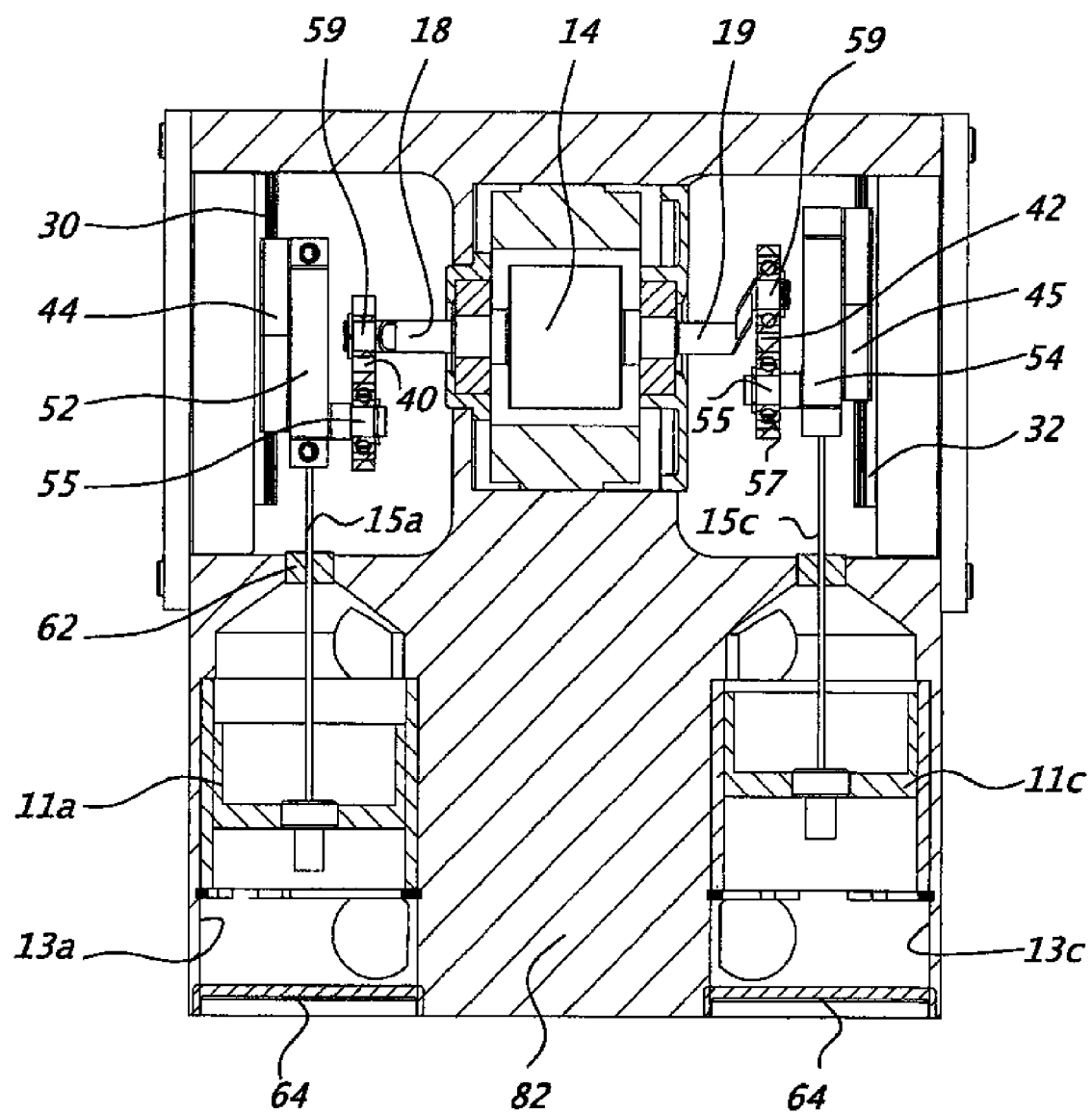
FIG. 9 is a cross-sectional view similar to FIG. 7 illustrating a different position of the reciprocating drive apparatus and associated pistons.

In FIG. 6, the reciprocating drive apparatus 60 is mounted in the upper portion of reduced size housing 82 in exactly the same way as it was mounted in a central portion of the housing 12 in the previous embodiment, and is linked to the piston rods 15 to drive the two pistons 11A and 11C to reciprocate back and forth in their respective cylinders. FIGS. 7 to 9 are simplified diagrammatic views of the reciprocating device apparatus 10 attached to two pistons for simplicity. In these Figures, each slide member and associated connecting plate is simplified to a single, unitary slide member with a mounting portion for the respective connecting rod. These drawings also illustrate the ball bearing connections or rotary bearings 57 between connecting link 42 and the pivot pin 55 of the slide member/connecting plate, and between the connecting link 42 and the pivot pin 59 at the end of the crank shaft 19. Similar connections are provided between the other connecting link 40 and the slide member and crank shaft 18.

FIGS. 7 and 8 illustrate the piston 11C at one end of its stroke, at the upper end of the glass tube 65 in which it slides. In this position, slide member 45 will be at one end position of its axial stroke on slide rail 32, specifically the upper end as viewed in FIG. 7. The piston 11A at this point is at a mid point in its stroke, traveling towards one end of the tube 65, with the slide member 44 at a mid point in its travel along slide rail 30. In FIG. 9, piston 11C has traveled to the opposite end of its stroke, at the lower end of tube 65, while piston 11A has returned to the mid-point of its stroke traveling towards the opposite end of its glass tube 65.

In each of the above embodiments, rotation of each crank shaft 18, 19 causes the associated connecting link 40,42 to rotate about pivot connection 55 due to rotation of the offset end of the crank shaft about the axis of rotation of crank shaft 18, 19, while the pivot connection 59 rotates relative to the end of the link to which it is connected. At the same time, the connecting link pulls the associated slide member up and down the linear bearing slide rail on which it is constrained to travel. This provides a relatively simple mechanism for converting rotational motion into true linear motion with little or no side loads.

Although the reciprocating drive apparatus of FIGS. 1 to 9 is used to convert rotational motion of a rotary drive into linear motion, it could alternatively be reversed with a linear drive connected to the linear bearing and the crank shafts linked to a device to be rotated. The pump assembly using the reciprocating drive may be used to pump any type of fluid, but is particularly intended for pumping gases for use in medical and other applications, for example a ventilator pump for supplying air or oxygen to a patient. The reciprocating drive apparatus may alternatively be used to drive a suction pump, an automobile or airplane pump, or in any other applications where it is necessary to convert rotational into linear motion, or vice versa.

The reciprocating drive apparatus of this invention is particularly useful in applications requiring a relatively small pump, such as medical equipment where the pump must be small enough to fit into the limited space available. Such pumps are also required to be low maintenance and cannot use lubricants. This means that there is little tolerance for side loads which often occur in existing reciprocating drives. This invention converts rotational to linear motion using a miniature linear bearing which is the key to delivering linear motion substantially free of any side loads to the piston. The drive apparatus has the capability of driving up to four pistons simultaneously, further reducing size requirements.

Although some exemplary embodiments of the invention have been described above by way of example only, it will be understood by these skilled in the field that modifications may be made to the disclosed embodiments without departing from the scope of the invention, which is defined by the appended claims.

What is claimed is:

1. A reciprocating drive apparatus, comprising:
  a housing;
  a rotational drive mounted in the housing, the rotational drive having opposite first and second ends;
  a first crank shaft having a first portion coupled to the first end of the rotational drive for rotation about an axis of rotation and a second portion offset from the first portion and axis of rotation;
  a second crank shaft having a first portion which is coupled to the second end of said rotational drive for rotation about said axis of rotation and a second portion offset from the first portion of said second crank shaft;
  a first reciprocating member mounted in the housing for linear movement along a first longitudinal axis;
  a second reciprocating member is mounted in the housing for linear movement along a second longitudinal axis parallel to the first longitudinal axis;
  a first linear bearing assembly secured in the housing to extend in a direction parallel to the first longitudinal axis;
  the first linear bearing assembly comprising a first linear guide rail and a first linear slide member having an inner portion slidably mounted for reciprocal movement along the first linear guide rail between opposite end portions and an outer portion aligned with said first longitudinal axis, the outer portion having opposite first and second ends and the first end being linked to said first reciprocating member;
  a first link arm having a first end rotatably linked to the second portion of the first crank shaft and a second end rotatably linked to the first linear slide member, whereby rotation of the first crank shaft forces the first linear slide member to slide back and forth on said first linear guide rail;
  a second linear guide rail is secured in the housing facing the second crank shaft and parallel to the second longitudinal axis, a second linear slide member slidably mounted on the second linear guide rail and having a first end coupled to said second reciprocating member, and
  a second link arm having a first end rotatably linked to the second portion of said second crank shaft and a second end rotatably linked to said second linear slide member, whereby rotation of said first and second crank shafts causes said first and second reciprocating members to reciprocate simultaneously along said first and second longitudinal axes, respectively.

2. The apparatus as claimed in claim 1, wherein the second linear slide member has an inner bearing portion which is slidably engaged and constrained on the second linear guide rail and an outer portion aligned with said second longitudinal axis, the outer portion of the second linear slide member having opposite first and second ends and the first end being linked to said second reciprocating member.

3. The apparatus as claimed in claim 2, wherein the inner portion of the first linear slide member comprises a first generally C-shaped bearing member for sliding engagement over the first linear guide rail, and the outer portion comprises a first separate connecting block rigidly secured to said first generally C-shaped bearing member, and the inner portion of the second linear slide member comprises a second generally C-shaped bearing member for sliding engagement over the second linear guide rail, and the outer portion comprises a second separate connecting block rigidly secured to said second generally C-shaped bearing member.

4. The apparatus as claimed in claim 1 wherein the housing has a first cylinder and the first reciprocating member comprises a first piston slidably mounted in the first cylinder, the first cylinder having an end wall adjacent the first linear slide member, the end wall having an opening aligned with the first longitudinal axis of movement of the first piston, and a first piston rod extending out of the first cylinder through the end wall opening and being secured to the first end of the outer portion of the first linear slide member.

5. The apparatus as claimed in claim 4, further comprising a seal in said end wall opening, the first piston rod extending through said seal.

6. The apparatus as claimed in claim 4, wherein the housing has a second cylinder aligned with the first cylinder and located at the opposite end of the first linear guide rail from the first cylinder, the second cylinder having an end wall adjacent an end of the first linear guide rail, and a second piston is slidably mounted in the second cylinder, a second piston rod extending from said second piston through said end wall, the second piston rod being secured to the second end of the outer portion of the first linear slide member, whereby linear movement of said first linear slide member along said first liner guide rail simultaneously reciprocates said first and second pistons in their respective cylinders.

7. The apparatus as claimed in claim 1, wherein the first crank shaft has an outer end offset from the outer end of the second crank shaft so that the stroke of the first reciprocating member on rotation of said first and second crank shafts is offset from the stroke of the second reciprocating member.

8. The apparatus as claimed in claim 1, further comprising a third reciprocating member aligned with said first longitudinal axis and coupled to the second end of the first linear slide member, and a fourth reciprocating member aligned with said second longitudinal axis and coupled to the second end of the second linear slide member, whereby rotation of the first and second crank shafts simultaneously causes the first, second, third and fourth reciprocating members to move along their respective axes.

9. The apparatus as claimed in claim 8, wherein the housing has a first pair of cylinders aligned along said first longitudinal axis and a second pair of cylinders aligned along said second longitudinal axis, the first reciprocating member comprising a first piston slidably movable in one of said first pair of cylinders, the second reciprocating member comprising a second piston slidably movable in one of said second pair of cylinders, a third piston is slidably movable in the other of said first pair of cylinders and a fourth piston is slidably movable in the other of said second pair of cylinder, the first and third piston each having a piston rod which is coupled to the first liner slide member, and the second and fourth piston each having a piston rod which is coupled to the second linear slide member.

10. The apparatus as claimed in claim 1, wherein the first linear guide rail faces said first crank shaft and extends in a direction transverse to said axis of rotation.

11. A reciprocating pump assembly, comprising:
a housing;
a first cylinder in the housing having a first longitudinal axis;
a first piston slidably mounted in the first cylinder for reciprocating movement along said first longitudinal axis;
a first piston rod extending from the first piston out of a first end of the first cylinder;
a first linear bearing assembly in the housing adjacent the first end of the first cylinder extending in a direction parallel to the first longitudinal axis, the first linear bearing assembly comprising a first linear slide rail secured to said housing and a first slide member slidably mounted on the first linear slide rail and having a first end rigidly secured to the first piston rod;
a rotational drive device in the housing having opposite first and second ends and an axis of rotation which extends transverse to said first longitudinal axis, the rotational drive device having a first crank shaft which has a first portion extending from the first end of said rotational drive device along said axis of rotation towards the first liner bearing assembly and a second portion offset from said first portion;
a first link member having one end rotatably connected to the second portion of the first crank shaft and the other end rotatably linked to the first slide member, whereby rotation of the first crank shaft forces the first slide member to move back and forth along the first linear slide rail between opposite end positions and to actuate the first piston to slide back and forth in the first cylinder;
a second cylinder in said housing having a second longitudinal axis parallel to the first longitudinal axis, the second cylinder being located on the opposite end of the rotational drive device from said first cylinder;
a second piston slidably mounted in the second cylinder, the second piston having a second piston rod extending out of a first end of the second cylinder;
the rotational drive device having a second crank shaft having a first portion extending from the second end of the rotational drive device along the axis of rotation in the opposite direction to the first crank shaft and a second portion offset from the axis of rotation;
a second linear bearing assembly in the housing adjacent the first end of the second cylinder extending in a direction parallel to the second longitudinal axis, the second linear bearing assembly facing the first linear bearing assembly and comprising a second linear slide rail secured to said housing and a second slide member slidably mounted on the second linear slide rail and having a first end rigidly secured to the second piston rod; and
a second link member rotatably linked at one end to the second end of the second crank shaft and at the other end to the second slide member, whereby rotation of the first and second crank shafts simultaneously causes the first and second pistons to reciprocate in their respective first and second cylinders.

12. The assembly as claimed in claim 11, wherein the housing has a third cylinder facing and aligned with the first cylinder and a fourth cylinder facing and aligned with the second cylinder adjacent the opposite ends of the first and second linear bearing assemblies, respectively, from the first and second cylinders, a third piston slidably mounted in said third cylinder with a third piston rod extending out of the third cylinder and coupled to the second end of the first slide member, and a fourth piston slidably mounted in said fourth cylinder with a fourth piston rod extending out of the fourth cylinder and coupled to the second end of the second slide member, whereby rotation of the first and second crank shafts simultaneously causes the first, second, third and fourth pistons to reciprocate in their respective cylinders.

13. A method of convening rotational motion to linear motion, comprising the steps of:
connecting a first end of the output of a rotational drive mounted in a housing and defining a first axis of rotation to a first portion of a first crank shaft;
rotatably connecting a second portion of the first crank shaft which is offset from the first portion and first axis of rotation to a first end of a first link arm;
connecting a second end of the output of the rotational drive to a first portion of a second crank shaft;
rotatably connecting a second portion of the second crank shaft which is offset from the first portion of the second crank shaft and the first axis of rotation to a first end of a second link arm;
rotatably connecting a second end of the first link arm to a first linear slide member of a first linear bearing assembly having a first linear guide rail secured in the housing to extend in a direction parallel to a first longitudinal axis, an inner portion of the first linear slide member being slidably mounted on the first linear bearing guide rail for movement back and forth along the first linear guide rail in a linear path, whereby rotation of the first crank shall through one complete revolution drives the first linear slide member to slide back and forth on said first linear guide rail between opposite end positions;
connecting the first end of an outer portion of the first linear slide member to a first reciprocating member mounted in the housing to be driven back and forth in a linear path along the first longitudinal axis;
rotatably connecting a second end of the second link arm to a second linear slide member slidably mounted on a second linear guide rail for movement back and forth along the second linear guide rail, the second linear guide rail being secured in the housing facing the second crank shaft, whereby rotation of the second crank shaft through one complete revolution drives the second linear slide member to slide back and forth on said second linear guide rail between opposite end positions; and
connecting the first end of the second linear slide member to a second reciprocating member mounted in the housing to be driven back and forth in a linear path along a second longitudinal axis parallel to the first longitudinal axis;
whereby rotation of said first and second crank shafts causes the first and second reciprocating members to reciprocate simultaneously along said first and second longitudinal axes, respectively.

* * * * *

UNITED STATES PATENT AND TRADEMARK OFFICE
CERTIFICATE OF CORRECTION

PATENT NO. : 7,654,802 B2 Page 1 of 1
APPLICATION NO. : 11/315608
DATED : February 2, 2010
INVENTOR(S) : Crawford, Jr. et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1076 days.

Signed and Sealed this

Twenty-third Day of November, 2010

David J. Kappos
*Director of the United States Patent and Trademark Office*